(12) United States Patent
Kühn et al.

(10) Patent No.: US 6,540,715 B1
(45) Date of Patent: Apr. 1, 2003

(54) METHOD AND DEVICE FOR IN-SITU FORMULATION OF A MEDICINAL SOLUTION FOR PARENTERAL APPLICATION

(75) Inventors: Bernd Kühn, Köln (DE); Georg Wiessmeier, Bergisch Gladbach (DE); Roland Rupp, Bergisch Gladbach (DE); Bernd Krumbach, Leverkusen (DE); Lothar Weismantel, Köln (DE); Erhard Herrmann, de Mexico (MX); Jürgen Klein, Kürten (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/582,245

(22) PCT Filed: Dec. 9, 1998

(86) PCT No.: PCT/EP98/08014

§ 371 (c)(1),
(2), (4) Date: Aug. 3, 2000

(87) PCT Pub. No.: WO99/32175

PCT Pub. Date: Jul. 1, 1999

(30) Foreign Application Priority Data

Dec. 22, 1997 (DE) .......................... 197 57 224

(51) Int. Cl.⁷ .............................................. A61M 37/00
(52) U.S. Cl. ..................................... 604/82; 366/162.4
(58) Field of Search .............................. 604/6.07, 6.14, 604/24, 82; 366/162.4, 162.5, 172.1, 173.1

(56) References Cited

U.S. PATENT DOCUMENTS

| | | | |
|---|---|---|---|
| 3,905,395 A | 9/1975 | Hupe | 137/604 |
| 4,261,521 A * | 4/1981 | Ashbrook | 241/5 |
| 4,802,630 A | 2/1989 | Kromrey et al. | 239/428 |
| 4,886,369 A | 12/1989 | Hankinson | 366/165 |
| 5,118,511 A * | 6/1992 | Horn et al. | 424/502 |
| 5,341,801 A * | 8/1994 | Zechner | 128/203.15 |
| 5,714,520 A | 2/1998 | Jones et al. | 514/731 |
| 5,885,216 A * | 3/1999 | Evans, III et al. | 600/431 |
| 6,248,087 B1 * | 6/2001 | Spears et al. | 604/6.14 |

FOREIGN PATENT DOCUMENTS

| | | | |
|---|---|---|---|
| DE | 2263769 | 2/1974 | B01F/5/06 |
| EP | 0560138 | 9/1993 | A61K/9/127 |
| EP | 0650739 | 3/1995 | A61M/5/14 |
| GB | 1472793 | 4/1977 | A61K/31/05 |
| GB | 2107191 | 4/1983 | A61M/5/14 |

* cited by examiner

Primary Examiner—David J. Walczak
Assistant Examiner—Peter deVore

(57) ABSTRACT

Method for the in situ formulation of a medicinal substance solution for parenteral administration, in which at least two metered part-streams are continuously combined with the aid of a mixer to an active ingredient-containing total volumetric flow, characterized in that the resulting medicinal substance solution is not in thermodynamic equilibrium, and in that the resulting total volumetric flow after mixing is 0.2 ml/h to 500 ml/h, preferably 5 ml/h to 500 ml/h, an apparatus for carrying out the method, and an active ingredient administration kit which contains the apparatus.

36 Claims, 3 Drawing Sheets

Figure 1:
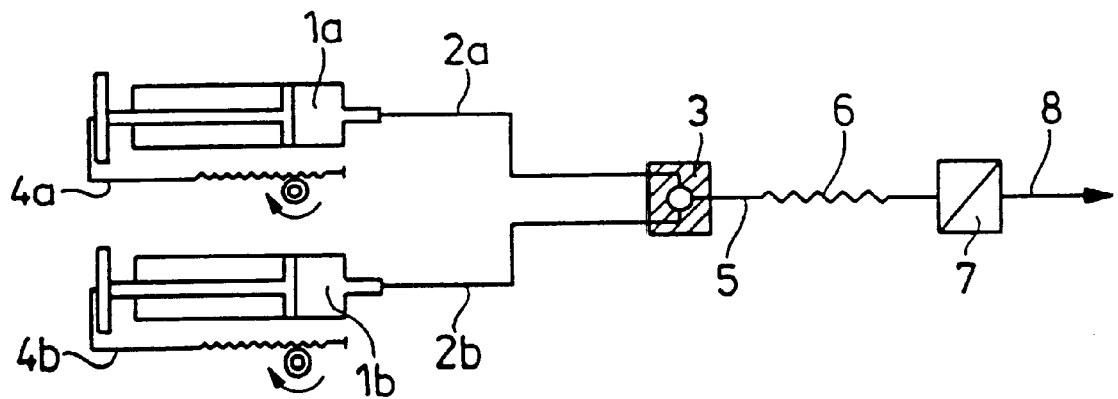

METHOD AND DEVICE FOR IN-SITU FORMULATION OF A MEDICINAL SOLUTION FOR PARENTERAL APPLICATION

The aim of developing infusion solutions which can be administered intravenously is always good tolerability of the preparation. To ensure this it is necessary for the formulation to be approximated as closely as possible to physiological circumstances, that is to say it should be in the form of an aqueous formulation with isotonic (osmolarity) and isohydric (pH) properties.

Some active pharmaceutical ingredients have the disadvantage that they are difficult to formulate or convert into a form ready for use owing to their low solubility, sensitivity to hydrolysis or oxidation or owing to their photosensitivity. This can in the final analysis be attributed to the fact that the active ingredients are not in thermodynamic equilibrium under usual formulating conditions, that is to say that they either precipitate or decompose under physiological conditions. Thus the formulation possibilities and, in the final analysis, the provision of such active ingredients are greatly restricted.

Active pharmaceutical ingredients, especially those of the more recent generation, often have the disadvantage of low solubility in aqueous medium at physiologically tolerated pH values. This applies in particular to active ingredients from the group of dihydropyridines, anaesthetics, antibiotics, antimycotics, immunosuppressants, CNS-active drugs, oncologicals, steroids, barbiturates and vitamins. Slightly soluble active ingredients have, according to the definition in current pharmacopoeias, a solubility in water of less than 1 percent by weight. Slightly soluble active ingredients frequently confront the pharmaceutical technologist with the problem of developing a sufficiently well tolerated aqueous infusion solution when the volume administered by infusion is strictly limited. The patient in particular in intensive care units (ICU) frequently receives several infusion solutions administered in parallel, in which case the acceptable daily volume depends on the kidney function of the individual. One priority of pharmaceutical development is to minimize the infusion volume, this parameter showing a contrary behaviour to the solubility of the substance. Formulating additions such as isotonicizing agents, antioxidants etc. moreover reduce the dissolving capacity of water. The active ingredient also frequently has a solubility or stability optimum outside the physiological pH range of 7.2–7.6, so that the formulation possibility is further restricted at the optimum pH.

Because of the poor solubility in aqueous media, the active ingredient is dissolved in an organic or aqueous/organic solvent or at strongly acidic/alkaline pH values in aqueous or aqueous/organic medium (active ingredient concentrate). In order to ensure tolerability, administration of this active ingredient concentrate must be preceded by dilution with an aqueous medium (diluting medium) or adjustment to physiologically tolerated pH values. This may result in supersaturated solutions. These are characterized in that the dissolved active ingredient is present in a concentration higher than is possible in the solvent at the given temperature by dissolving the active ingredient crystals. Such solutions are, as a consequence of the kinetic inhibition of crystallization, initially optically clear and virtually free of particles. However, the solutions are thermodynamically unstable. Thus, over the course of time, they lead to the active ingredient crystallizing out and thus particles being formed. Since relatively long times, which include at least the duration of the infusion, frequently elapse for example after preparation of such solutions in hospitals until they are completely infused into the patients, formation of particles in the solution is possible during this. Particles injected into the bloodstream may, however, depending on their size and shape lead inter alia to vascular occlusion and thus to serious harm to the patient. This risk can be reduced either by ensuring the stability of the supersaturation also over a lengthy period and under all environmental conditions, demonstrating this with certainty, or by minimizing the time the supersaturated solution stands after its preparation. The latter object is achieved by the present invention, namely by preparing the supersaturated solution from an active ingredient concentrate and a diluting medium with use of a special mixer immediately before administration—on the patient's arm—and only seconds up to a few minutes elapsing until the solution enters the bloodstream.

On simultaneous parenteral administration of different solutions by intravenous infusion so-called connecting pieces or Y pieces (for example Codan Art. No. C87/2R) have been used to date. Connection to other infusion equipment takes place, for example, via so-called Luer-Lock connectors complying with DIN 13090 Part 2 (disposable medical articles: medical products; standards and other documents; Beuth Verlag 1989). The infusion solutions having viscosities in the region of a few mPas are fed from different containers to the relevant connecting piece and combined therein simply by being conducted together before the mixture reaches the patient. An infusion device of this type is described, for example, in DE-3228595-C2. In this case, 2 solutions from infusion bottles are combined by gravity through a Y piece and infused. Disposable articles of this type are commercially available in a variety of forms. The disadvantage of the available devices is that it is impossible to mix fluid media with very different viscosities at the available low flow rates (5–500 ml/h) sufficiently and quickly enough because the commercially available connecting pieces are not optimal in terms of their function as mixers. In particular at low flow velocities there is sometimes a back-flow of the solutions, and components of the solution spend some time in regions of low flow (dead spaces). This can lead to crystallization inside the administration system. Organic solvents which can be administered parenterally may have viscosities above 100 mPas (for example macrogol 400). When the organic active ingredient concentrate and the aqueous diluting medium are mixed there is a risk that the active ingredient will crystallize out of the supersaturated solution after a certain time. The time up to the onset of crystallization decreases with increasing content of aqueous phase. However, at the same time, the tolerability increases with increasing content of aqueous phase.

The result of the problems described is that no such concentrate/dilution systems have yet been developed for a marketable product. On the contrary, the only solution presentations marketed are those whose system is not supersaturated. This is achieved, for example, by adding relatively large amounts and relatively high concentrations of organic solvents (ethanol, macrogol, propylene glycol etc.) or solubilizers and surfactants (Tween, Cremophor), which have an adverse effect on the local and systemic tolerability of the formulation.

GB-A-1472793 describes such formulations for the anaesthetic propofol, in which surface-active substances and water-miscible, nonaqueous solvents are added to the aqueous base. A concentration of 20–30% of organic medium should not be exceeded as limits for the local tolerability of organic solvents in infusions. The systemic tolerability of the solvents varies in a substance-specific manner. In general, solvents lead to irritation and inflammation of veins and to haemolysis. Surfactants have even stronger haemolytic activity and, moreover, may cause an anaphylactic shock reaction with a fatal outcome. It is therefore necessary to examine such formulations particularly critically, and a precondition for a decision in their favour is an appropriate benefits/risk assessment.

Another possibility, for which the possible uses are, however, only limited, is to develop presentations such as, for example, lipid emulsions or liposome formulations, but these are considerably more complicated and thus more costly than conventional solution formulations. The formulation of oil-in-water emulsions for the active ingredient propofol is likewise described in GB 1 472 793 and furthermore in DE-19 509 828-A1. Further examples of slightly soluble active ingredients are to be found in U.S. Pat. No. 4,168,308. The production of aqueous liposome dispersions as a possible formulation of slightly soluble medicinal substances is described in EP-A-0 560 138 for active ingredients of the dihydropyridine class. This makes the considerable technical complexity of these alternative formulations clear.

If such formulation problems become evident, frequently no development of slightly soluble active ingredients is carried out, or the development times for a formulation become markedly prolonged.

It is an object of the invention to provide a method with which it is possible to administer slightly soluble active ingredients in a simple manner and, at the same time, distinctly reduce the amount and concentration of excipients necessary (solvents, surfactants etc.) for the formulation by comparison with conventional formulations, or make them entirely unnecessary. The intention is furthermore to provide an apparatus with which it is possible to mix an active ingredient concentrate in a very short time completely with a diluting medium so that the active ingredient can reach the patient's vein in dissolved form. The mixing apparatus to be developed for this purpose must meet additional requirements: the construction material chosen is expediently one which can be sterilized and with which no attrition takes place. The flow pathways are expediently designed and dimensioned so that no regions of low flow (dead spaces) result and the flow velocities produce vigorous mixing in the mixing apparatus even at low flow rates. In order to ensure that the infusion solution spends a short time between the mixing apparatus and the patient, the mixing apparatus should be attached in the vicinity of the infusion site. The pressure prevailing in the mixing apparatus should not exceed 1 bar.

The invention therefore relates to a method for the in situ formulation of a medicinal substance solution for parenteral administration, in which at least two metered part-streams are continuously combined with the aid of a mixer to an active ingredient-containing total volumetric flow, characterized in that the resulting medicinal substance solution is not in thermodynamic equilibrium, and in that the resulting total volumetric flow after mixing is 0.2 ml/h to 500 ml/h, preferably 5 ml/h to 500 ml/h.

A medicinal substance solution which is not in thermodynamic equilibrium within the meaning of the invention is a solution which, under the administration conditions, has a tendency to undergo a transition with a chemical or physical change into a lower-energy state. Such a chemical or physical change may consist of, for example, the active ingredient decomposing, for example through hydrolysis, oxidation or photolysis, or being precipitated. The formulation of the medicinal substance solution by combining the metered part-streams in the method of the invention takes place in such a way that the resulting medicinal substance solution is subject to no change compromising administration until it enters the human body.

In a preferred embodiment of the method, the two part-streams are combined in a mixing chamber volume of 0.2 µl to 2 µl, preferably 0.4 µl to 1.5 µl.

In another preferred embodiment of the method of the present invention, the metered part-streams comprise at least one active ingredient-containing solution and at least one active ingredient-free diluting medium, and the resulting solution, which is not in thermodynamic equilibrium, is a supersaturated medicinal substance solution.

The active ingredient-containing solution is preferably an organic or aqueous organic active ingredient concentrate, and the active ingredient-free diluting medium is an aqueous or aqueous organic diluting medium.

The active ingredient concentrate is formulated using suitable water-miscible organic solvents, mixtures thereof or mixtures with water, in each of which the particular active ingredient dissolves especially well. Preferred organic solvents are macrogols of various molecular weights, 1,2-propylene glycol, ethanol, glycerol, glycofurol, 2-pyrrolidone and glycol ethers. It is possible to add further excipients such as stabilizers (surfactants, complexing agents) or antioxidants, isotonicizing agents, agents to adjust the pH, inter alia, to the active ingredient concentrate. However, it is preferred not to add stabilizers or at least to considerably reduce the amount thereof. It is possible by choosing the optimal solvent advantageously to reduce the total amount of organic solvent required. The active ingredient concentrate should not exceed a viscosity of 500 mPas and is preferably in the range 50–150 mPas, in order to ensure the function of the mixer. Solvents of higher viscosity such as glycerol and higher molecular weight macrogols are therefore mixed with lower viscosity solvents such as ethanol, water, 1,2-propylene glycol or others.

The active ingredient concentrate is diluted using diluting media. These are water, physiological saline or other electrolyte solutions such as Ringer solution, Ringer lactate solution etc., glucose-, sorbitol-, mannitol- or other carbohydrate-containing solutions, volume replacement solutions (dextrans and derivatives thereof, gelatin and derivatives thereof, starch derivatives), serum derivatives and combinations or aqueous organic solvent mixtures with solvent concentrations of less than 30%, preferably less than 10%. Suitable solvents are the water-miscible solvents already mentioned, such as macrogol of varying molecular weight, 1,2-propylene glycol, ethanol, glycerol, glycofurol, 2-pyrrolidone and glycol ethers. It is possible to add further excipients such as stabilizers (surfactants, complexing agents) or antioxidants, isotonicizing agents, agents to adjust the pH, inter alia, to the diluting medium. However, it is preferred not to add stabilizers or at least to considerably reduce the amount thereof. The viscosity of the diluting medium is preferably in the range 1–10 mPas, because this reduces the viscosity of the complete mixture and that of blood is approached.

For the purpose of the present invention, the supersaturated medicinal substance or active ingredient solution formed on mixing the active ingredient concentrate and diluting medium contains more dissolved active ingredient than the maximum amount of active ingredient which can be taken up by a solution of the same volume in thermodynamic equilibrium at the same temperature. The latter is the solubility of the active ingredient in the resulting infusion solution at the given temperature.

The result of mixing active ingredient concentrate and diluting medium is an infusion solution of the desired concentration, in which the active ingredient is present in dissolved but supersaturated form and does not crystallize out over the period from mixing until entry into the vein. In the vein there is rapid dilution by the bloodstream and binding to plasma proteins, which acts to counter crystallization of the active ingredient there. The concentration of solvents in the complete solution can be reduced to distinctly less than 30%, and in some cases to 7%, leading to the expectation of good local tolerability. At the same time, the total volume of the infusion solution and thus the total amount of organic solvent and other excipients is kept low.

In a further embodiment of the invention, the active ingredient-containing solution is an aqueous or aqueous organic active ingredient concentrate, and the active ingredient-free diluting medium is an aqueous or aqueous organic diluting medium, the pH values of which are matched together so that the total volumetric flow resulting after the mixing has a physiologically tolerated pH in the range from 3 to 10, preferably 5–8.

This embodiment is used in cases where the active ingredient has a pH-dependent solubility or stability, and the solubilities or stabilities are good only in nonphysiological pH ranges below pH 3 and above pH 10. An appropriately acid or alkaline aqueous or aqueous organic active ingredient concentrate is then prepared.

It is preferable to add to the active ingredient concentrate further excipients such as stabilizers (surfactants, complexing agents, solubilizers), water-miscible organic solvents or antioxidants, isotonicizing agents, buffering agents and others. However, it is preferred not to add stabilizers and organic solvents or at least to considerably reduce the amount thereof.

Aqueous diluting media whose pH has in each case been adjusted to counter the active ingredient concentrate are used to dilute the acidic or alkaline active ingredient concentrate. These diluting media are water, physiological saline or other electrolyte solutions such as Ringer solution, Ringer lactate solution etc., glucose-, sorbitol-, mannitol- or other carbohydrate-containing solutions, volume replacement solutions (dextrans and derivatives thereof, gelatin and derivatives thereof, starch derivatives), serum derivatives and combinations or aqueous organic solvent mixtures with solvent concentrations of less than 30%, preferably less than 10%. Suitable solvents are the water-miscible solvents already mentioned, such as macrogol of varying molecular weight, 1,2-propylene glycol, ethanol, glycerol, glycofurol, 2-pyrrolidone and glycol ether. It is possible to add further excipients such as stabilizers (surfactants, complexing agents) or antioxidants, isotonicizing agents, buffering agents, inter alia, to the diluting medium. However, it is preferred not to add stabilizers or at least to considerably reduce the amount thereof. The viscosity of the diluting medium is preferably in the range 1–10 mPas, because this reduces the viscosity of the complete mixture and that of blood is approached.

The combination of the active ingredient concentrate and diluting medium results in the pH of the complete solution being maintained at physiologically tolerated pH values in the range from 3 to 30, preferably in the range from 5 to 8.

The method of the invention is particularly suitable for the administration of active ingredients having a solubility of less than 1% by weight in water at 20° C.

The active ingredient is preferably selected from the group consisting of dihydropyridines, anaesthetics, antibiotics, antimycotics, immunosuppressants, CNS-active drugs, oncologicals, steroids, barbiturates and vitamins.

Examples of such active ingredients are paclitaxel, docetaxel or substances related thereto, or ciclosporin.

The method is implemented by employing a mixer which preferably has no dead spaces and particularly preferably is miniaturized and has no dead spaces. The time spent by the mixture in the mixer and mixing section is expediently less than 1 min, preferably less than 30 s. The mixer expediently used is a nozzle mixer in which each of the part-streams is passed through a nozzle with a hydraulic diameter between 1 $\mu$m and 500 $\mu$m, preferably between 100 $\mu$m and 250 $\mu$m, and then collide with velocity components in opposite directions in a mixing chamber, and the mixture which forms is conveyed away as total volumetric flow. The total volumetric flow is expediently conveyed away through at least one aperture downstream of the mixing chamber. The nozzle diameter is expediently chosen so that the flow velocity in the nozzles is 0.01 to 15 m/s, preferably 0.01 to 3 m/s.

The invention furthermore relates to an apparatus for the in situ formulation of a medicinal substance solution for parenteral administration, having at least two feed lines, in each of which a reservoir and a metering device are connected in series, and the feed lines open downstream of the metering devices into an infusion line, characterized in that the feed lines are connected to a nozzle mixer which consists of a mixing chamber connected to the infusion line and of two nozzles which are disposed in the feed lines, are opposite to one another and open into the mixing chamber.

The mixing chamber has a volume of, preferably, 0.2 $\mu$l to 2 $\mu$l, particularly preferably of 0.4 $\mu$l to 1.5 $\mu$l, and the nozzles have a hydraulic diameter of, preferably, 1 $\mu$m to 500 $\mu$m, particularly preferably of 100 $\mu$m to 250 $\mu$m.

It is expedient for a homogenizing aperture with a hydraulic diameter of 1 to 500 $\mu$m, preferably 100 to 250 $\mu$m, to be disposed at the outlet from the mixing chamber.

The flow pathways within the two feed lines, including the metering devices and the nozzles, are preferably designed symmetrically.

The nozzle mixer preferably consists of an injection-mouldable plastic, particularly preferably of polycarbonate. When the apparatus according to the invention is used with photosensitive active ingredients, a substance which ensures adequate protection from light even with thin mixer walls can be admixed with the plastic. The substance is expediently selected in this case so that it effectively shields from the wavelength range in which the photosensitive active ingredient is decomposed.

The invention furthermore relates to an active ingredient administration kit for carrying out the method according to the invention, consisting of a pack with the apparatus according to the invention and of a reservoir at least for the active ingredient concentrate. The active ingredient administration kit preferably additionally contains tubing lines for the connections to the apparatus (mixer) and to the metering devices. Concerning the active ingredients, the active ingredient concentrates and the diluting media, reference may be made to the statements above.

Figure 4:
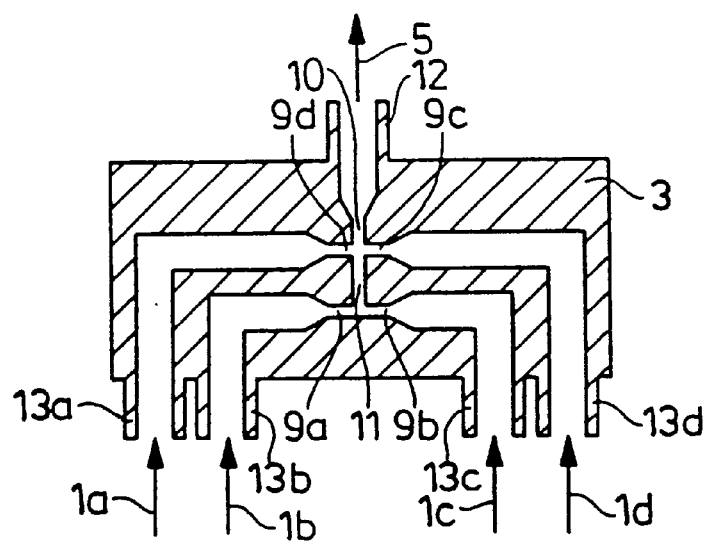
Figure 5:
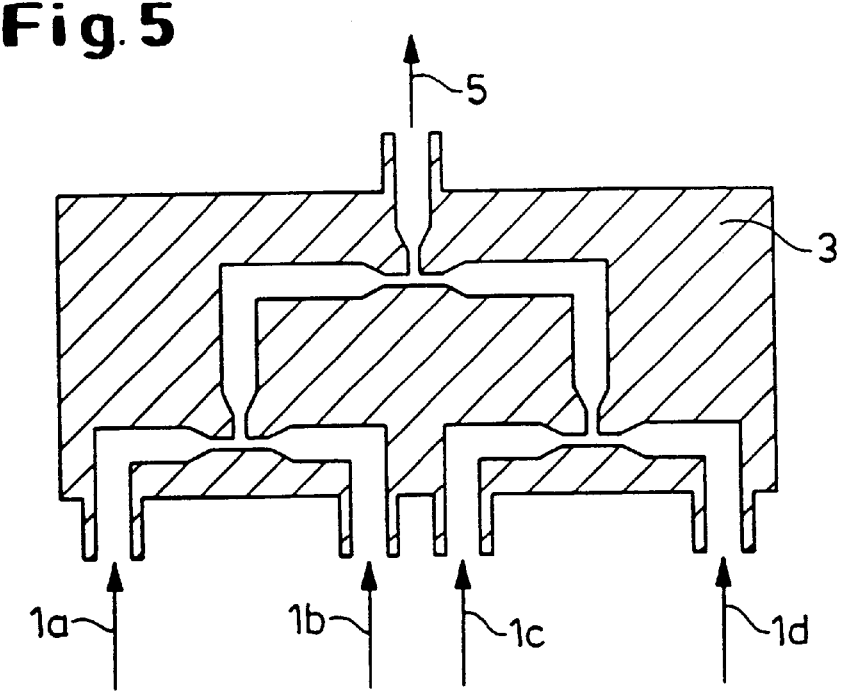

The invention is described in detail hereinafter by means of exemplary embodiments and drawings. These show:

FIG. 1 a basic procedure diagram for carrying out the formulation method according to the invention for parenteral administration, FIG. 2 a preferred embodiment of a nozzle mixer for mixing and homogenizing an active ingredient concentrate and a diluting medium, FIGS. 3–5 further embodiments of the nozzle mixer and FIG. 6 an experimental apparatus for carrying out the exemplary embodiments described hereinafter.

In the embodiment shown in FIG. 1, the active ingredient concentrate (1a) and the diluting medium (1b) are fed by syringe drivers or infusion pumps (4a, 4b) through the tubing connectors to the apparatus (3). The mixture (5) is fed immediately after the mixing in the apparatus (3) according to the invention, and after passing through the connecting tubing (6) and, where appropriate, a filter (7) and the injection needle (8), to the patient.

Instead of these syringe drivers or infusion pumps it is also possible to employ other suitable systems such as, for example, two separate syringes which are connected to the mixing apparatus and are operated manually, for example for administering a bolus injection. In this case, the maximum flow rate of the part-streams and the maximum pressure in the system essentially depend on the manually applied force, it being necessary to take account of the tolerability of the administration.

Figure 2:
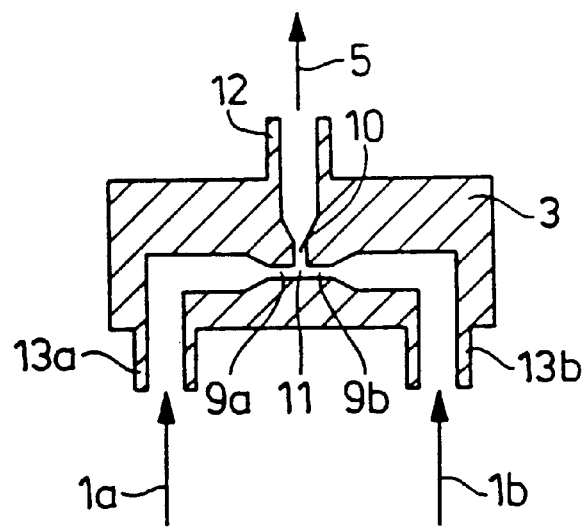

The embodiment of the apparatus according to the invention shown in FIG. 2 consists of at least one nozzle (9a or 9b) and of a homogenizing aperture (10) downstream in the direction of flow, which can be in any suitable relative geometric arrangement, of a mixing chamber (11) and of a mixing section (12). The connecting tubing (6) can also serve as mixing section. The nozzles (9) disperse the respective starting fluids (1a, 1b) and feed them to the mixing chamber (11). The task of the downstream aperture (10) is to homogenize the resulting mixture. The mixing section (12) serves additionally to ensure complete mixing before the mixture is injected into the patient. Two opposing nozzles (9a, 9b) are preferably used for mixing two fluids (FIG. 2); the homogenizing aperture (10) is dispersed perpendicularly and symmetrically with respect to the nozzles (9a, 9b) on the mixing chamber (11). An essential precondition for achieving the required object of mixing is to minimize the mixing chamber volume (mixing chamber (11)) between nozzles (9a, 9b) and homogenizing aperture (10) in order to maximize the energy input per volume. Thus, miniaturized construction of the complete apparatus is particularly suitable. The total void volume is, for example, 0.5 $\mu$l. The orifices of the nozzles and of the aperture have a diameter between 0.001 and 0.5 mm, preferably 0.25 mm. The total pressure drop is then, with fluid velocities in the nozzles of 0.1 m/s to 15 m/s, less than 1 bar. An apparatus according to the invention is fabricated in a flat design preferably from polycarbonate and preferably has edge dimensions of 1 cm×1 cm×0.4 cm (L×B×H), so that it can in the method according to the invention be attached without difficulty in the direct vicinity of the injection site on the patient (adhesive plaster). For stabilizing the apparatus when attaching to the patient's arm it is additionally possible to provide so-called wings on the housing of the apparatus. An in-line arrangement was chosen for the tubing connections in order to reduce the mechanical stress on the housing of the apparatus. Appropriate standardized Luer-Lock connections can be attached at the ends of the tubing for connecting the apparatus according to the invention to syringe drivers or infusion pumps which convey in each case the initial fluids to be mixed.

Figure 3:
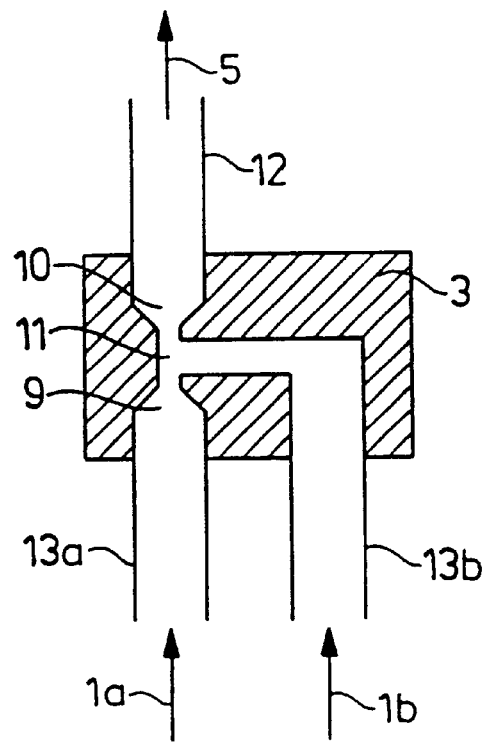

A further embodiment of the apparatus according to the invention which is depicted in FIG. 3 provides for feeding only one fluid, that of low viscosity, through a nozzle (9) which is arranged opposite the homogenizing aperture (10); however, in principle, all geometric arrangements can be implemented. Thus, it is possible because of the miniaturized construction for any number, but preferably less than 10, initial fluids to be fed to the apparatus, as depicted in FIG. 4 and in FIG. 5 by way of example for a total of four initial fluids (1a–1d). The embodiment shown in FIG. 5 is preferably used. The high degree of integration makes it possible easily to replicate many times the basic structure in the apparatus according to the invention (FIG. 5).

The method according to the invention, including the apparatus according to the invention, has the advantage that supersaturated infusion solutions can be prepared reliably and reproducibly and be administered immediately after preparation. This dispenses with the problems of the stability of the prepared infusion solution, which must amount to several hours in hospital procedures, so that it is possible for the first time also to perform intravenous administrations of supersaturated solutions of slightly soluble active ingredients routinely in hospital procedures. The direct administration makes it possible to achieve a distinctly reduced concentration and absolute amount, compared with conventional solutions, of solvents which impair the tolerability of the solution. There is also the potential to dispense with particular organic solvents (for example ethanol) in the infusion solution. This might make it possible to extend the market for some infusion solutions to countries in which the relevant solvent is not approved for parenteral administrations (for example Japan: ethanol). It is also possible to dispense with excipients which are normally added to the infusion solution for stabilization, or at least distinctly reduce the content thereof.

The apparatus according to the invention can be injection moulded, resulting in the possibility of economic mass production.

It is possible with the aid of the apparatus to mix very rapidly and completely fluids differing considerably in viscosity. This avoids local supersaturation occurring for lengthy periods, which would result in precipitation of the active ingredient. Local increases in the concentration of organic solvent, which may damage blood vessels, likewise do not occur.

In order to avoid damage to blood vessels it is necessary for the active ingredient concentrate to be homogeneously mixed in the diluting medium. Hence checking the mixing is an essential aspect for characterizing the apparatus according to the invention.

Figure 6:
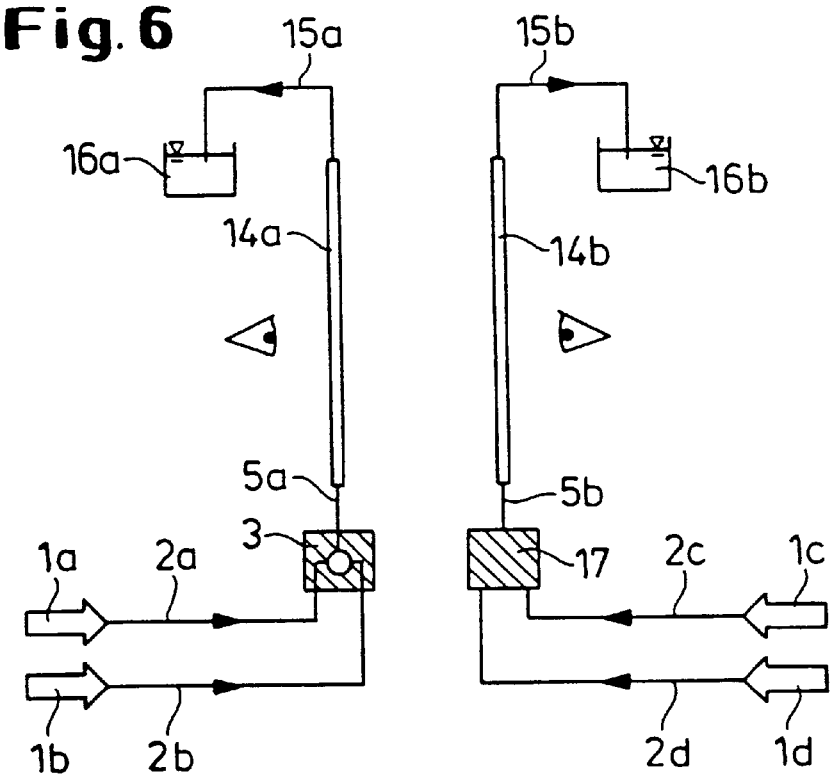

The experimental apparatus depicted diagrammatically in FIG. 6 was used to demonstrate the operability of the method according to the invention and apparatus according to the invention. The various types of mixer indicated in the following table were used for this:

| Mixer type | Diameter | | Volume of the mixing chamber $\mu$l |
|---|---|---|---|
| | Nozzles $\mu$m | Aperture $\mu$m | |
| A | 100 | 100 | 0.5 |
| B | 250 | 250 | 1.5 |
| C | CODAN Article No. C87/2R | | |

The experimental apparatus consists of two identical trains which make it possible to compare the apparatus according to the invention (3: mixer type A and B) directly with a conventional connecting piece (17: mixer type C). The active ingredient concentrates (1a, 1c) are fed with the aid of Perfusor pumps (use of 50 ml Perfusor syringes) through the tubing lines 2a, 2c (internal diameter 2 mm) to the apparatus (3) and the connecting piece (17). The metering of the diluting media (1b, 1d) likewise takes place through Perfusor pumps and tubing lines (2b, 2d). The mixtures (5a, 5b) leave the apparatus (3) and the connecting piece (17) and pass directly into the glass tubes 14a and 14b respectively (internal diameter 1.8 mm). The mixtures leave the glass tubes and are passed through tubings (15a, 15b) into collection vessels (16a, 16b).

To assess the mixed materials, an organic solvent approved for parenteral administration and having a viscosity of 100 mPas (macrogol 400) was used, specifically without active ingredient. The solvent was acidified with a few drops of HCl, and the diluting medium water (about 1 mPas) was made basic with NaOH and coloured red with phenolphthalein. The ratios of amounts were chosen so that decolorization occurred at the particular ratio of amounts of water and solvent. The colour change of the indicator used takes place between pH 8 and pH 10. Assessment of the mixed materials was based on the decolorization behaviour and the visual check of homogeneous phase mixing, and after what distance in the glass tubes (14) decolorization or homogeneous mixing is found.

Besides ensuring homogeneous mixing of active ingredient concentrate and diluting medium, a further aim was to adjusted depending on the mixing problem so that there are also nozzles or apertures with different diameters in a particular apparatus. The various exemplary embodiments are described below.

EXAMPLE 1

Experiments for the Assessment of the Mixing Materials

In the case of the apparatuses according to the invention (mixer type A and B) it emerged that the mixture (5) was already decolorized after emergence from the homogenizing aperture (10). Homogeneous mixing of the phases took place after passing through a mixing section (11) of a maximum of 20 mm in 0.4 and 17 seconds. After this time had elapsed, complete mixing of solvent and diluting medium is to be expected, thus avoiding vascular damage in the patient.

| Solvent | Volumetric flow [ml/h] | Diluting medium | Volumetric flow [ml/h] | Mixer type | Decolorization section[2] mm | Mixing section[2] mm | Time[3] s |
|---|---|---|---|---|---|---|---|
| PEG[1] | 1 | water | 10 | A | 0 | ≦20 | ≦17.00 |
| PEG[1] | 30 | water | 75 | B | 0 | ≦20 | ≦1.80 |
| PEG[1] | 30 | water | 400 | B | 0 | ≦20 | ≦0.43 |
| PEG[1] | 1 | water | 10 | C | >600 | ≧600 | ≧500.00 |
| PEG[1] | 30 | water | 75 | C | >600 | ≧600 | ≧53.00 |
| PEG[1] | 30 | water | 400 | C | >600 | ≧600 | ≧13.00 |

[1]PEG: macrogol 400;
[2]pathway in the glass tube with a diameter of 1.8 mm (see FIG. 6, 14a and 14b);
[3]time spent in the glass tube until mixing is homogeneous.

ensure that no active ingredient crystallizes out within a particular time and with a large content of diluting medium in the infusion solution. This was done by preparing various active ingredient concentrates, which were then mixed with the diluting medium in the manner described above in the apparatus (3) according to the invention. It was firstly found, by observing the mixture (5a) in the glass tube (14a), whether visible particles were present in the mixture (for example crystallization from supersaturated solution). If this was not the case, the mixture (5a) was passed immediately downstream of the apparatus (3) which had previously been detached from the glass tube, into a measuring vessel, and the particle distribution (HIAC) was determined. A sample volume of 10 ml was needed for this. Sampling and preparation for the measurement take about 10 min. This ensures that the mixture stands for at least 10 min, which is the maximum time between mixing and entry into the patient in one embodiment of the method according to the invention. The particle counts indicated in the tables for the respective examples were obtained by averaging three measurements. This made it possible to check whether the maximum particle concentrations specified in the pharmacopoeias (USP XXIII: The United States Pharmacopeia Jan. 23, 1995) were not exceeded. It is appropriate to use various types of apparatuses in order to ensure sufficiently good mixing in the entire volumetric flow range. The types differ in the diameter of the nozzles and apertures (see table above). Moreover, only nozzles and apertures with a uniform diameter are initially used in an apparatus. However, it is also possible for the diameters of nozzles and apertures to be individually In the case of the commercially available connecting piece (mixer type C), no mixing of diluting medium and solvent was detectable. Two streams of fluid, one coloured (diluting medium) and the other colourless (solvent), ran virtually through the entire glass tube (L=600 mm). In some regions of the glass tube there was partial turbulence of the streams of fluid without decolorization; complete mixing was not observed in this case.

EXAMPLE 2

Formulation of an Antibiotic of the Oxazolidinone Class (Bay 17-1648) with Glycofurol as 2% Strength Active Ingredient Concentrate The daily dose of the antibiotic Bay 17-1648 ((5S)-3-(3-methyl-2-benzothiazolinon-6-yl)-5-(propionylaminomethyl)oxazolidin-2-one, EP 738726) is about 1000 mg. The following data were found for the saturation concentration (M/V) at 20° C.:

| Solvent | Dynam. viscosity [mPas] | Saturation concentration | Volume of solvent per dose (1000 mg) |
|---|---|---|---|
| Water (W) | 1 | 0.045% (45 mg/100 ml) | 2222 ml |
| Propylene glycol (PG) | 60 | 0.7% (700 mg/100 ml) | 143 ml |

-continued

| Solvent | Dynam. viscosity [mPas] | Saturation concentration | Volume of solvent per dose (1000 mg) |
|---|---|---|---|
| Macrogol 400 (PEG) | 100–130 | 1.6% (1600 mg/100 ml) | 63 ml |
| Glycofurol (GF) | about 50 | 2.2% (2200 mg/100 ml) | 45 ml |

Taking the saturation concentrations as the basis for the formulations, the required volume of solvent for the daily dose of 1000 mg is at least 2222 ml W, 143 ml PG, 63 ml PEG or 45 ml GF. Since for a stable formulation it is necessary to keep a safety margin from the saturation concentration in order to ensure low-temperature stability as well, the solvent volumes mentioned are the lower limit for a conventional solvent formulation.

It is possible with GF to formulate a 2% strength active ingredient concentrate which must be diluted before use in order to be sufficiently well tolerated. The mixture ready for use with a maximum concentration of 20–25% GF requires, for administration in the hospital, physical stability in respect of crystallization for at least 6 h. Dilution experiments carried out in a conventional way with aqueous media without the use of the method according to the invention and the apparatus according to the invention showed the following result:

| Solvent concentration | 25% GF | 20% GF |
|---|---|---|
| Diluting medium | water | 20% strength glucose solution |
| Active ingredient saturation conc. in CM | ca. 200 mg/100 ml (0.2%) | ca. 100 mg/100 ml (0.1%) |
| Active ingredient concentration in CM | 500 mg/100 ml (0.5%) | 400 mg/100 ml (0.4%) |
| Supersaturation in CM | ca. 2.5-fold | ca. 4-fold |
| Amount of solvent per dose | 50 g/1000 mg | 50 g/1000 mg |
| Crystallization | after 1–2 h | after 1 h The 20% strength GF solution was poorly tolerated in animal experiments |

On use according to the invention of the mixing apparatus, 50 ml of 2% strength active ingredient concentrate (GF) and 667 ml of water (ratio 1:13) are combined by means of a Perfusor pump for the concentrate and infusion pump for the diluting medium through the apparatus so that a total volumetric flow of 430 ml/h is reached. This reduces the concentration of the organic solvent glycofurol in the complete mixture to 7%. The infusion volume needed to administer the daily dose of 1000 mg of Bay 17-1648 in this case is 717 ml/day. The infusion time in this case is about 100 min per 1000 mg of Bay 17-1648.

The saturation solubility of Bay 17-1648 with 7% GF in water is about 20 mg/100 ml. Compared with this value, the mixture ready for use is about 7-fold supersaturated at 140 mg/100 ml. As the particle measurements show, the formulation is stable to crystallization for at least 1 min.

| Mixer type | — | B |
|---|---|---|
| Inlet pressure: diluting medium (DM) | mbar | 100 |
| Inlet pressure: active ingredient concentrate (AC) | mbar | 120 |
| Solvent concentration (CM) | g/100 ml[1] | 7 |
| Active ingredient concentration in the solvent | g/100 ml[2] | 2 |
| Total amount of infused solvent | ml | 50 |
| Diluting medium | — | water |
| Volume of the complete mixture (CM) | ml | 717 |
| Metering rate (total active ingredient dose) | mg/min | 1000 mg/100 min |
| Volumetric flow CM | ml/b | 430 |
| Flow velocity: AC nozzle | m/s | 0.17 |
| Flow velocity: DM nozzle | m/s | 2.26 |
| Flow velocity: CM aperture | m/s | 2.43 |
| Particle count ≧ 10 μm [max. 25/ml] | Particle count/ml | 19 |
| Particle count ≧ 25 μm [max. 3/ml] | Particle count/ml | 1 |

[1]Mass of solvent based on 100 ml of complete solution;
[2]Mass of active ingredient based on 100 ml of solvent (active ingredient concentrate).

Whereas it was not possible to achieve adequate stability to crystallization of the mixture ready for use and satisfactory tolerability of the solution in the experiment on formulation of a conventional solvent formulation, the use according to the invention of the method and the apparatus made well-tolerated parenteral administration of the active ingredient possible.

EXAMPLE 3

Formulation of an Antibiotic of the Oxazolidinone Class (Bay 17-1648) with Macrogol 400 as 1.5% Strength Active Ingredient Concentrate The saturation solubility of the antibiotic Bay 17-1648 in macrogol 400 (PEG) permits, in analogy to Example 2, the formulation of a 1.5% strength active ingredient concentrate which must likewise be diluted before use. The mixture ready for use with a maximum concentration of 30% PEG requires, for administration in the hospital, physical stability in respect of crystallization for at least 6 h. Dilution experiments carried out in a conventional way with water without the use of the method according to the invention and the apparatus according to the invention showed the following result:

| Solvent concentration | 30% PEG | 17% PEG | 10% PEG |
|---|---|---|---|
| Diluting medium | water | water | water |
| Active ingredient saturation conc. in CM | 150 mg/100 ml (0.15%) | 100 mg/100 ml (0.1%) | 80 mg/100 ml (0.008%) |
| Active ingredient concentration in CM | 450 mg/100 ml (0.45%) | 250 mg/100 ml (0.25%) | 150 mg/100 ml (0.15%) |
| Supersaturation in CM | 3-fold | 2.5-fold | ca. 2-fold |
| Amount of solvent per dose | 66.7 g/1000 mg | 68 g/1000 mg | 66.7 g/1000 mg |
| Crystallization | after 24 h | after 1 h | after 1 h |

The 30% strength solvent concentration shows marginal local tolerability in animal experiments. Lower solvent concentrations show distinctly less stability to crystallization. It was moreover difficult, owing to the relatively high viscosity of the solvent, to obtain a homogeneous solution on mixing the components of the solution.

On use according to the invention of the mixing apparatus, 33.5 ml of 1.5% strength active ingredient concentrate (PEG) and 430 ml of water (ratio 1:13) are combined by means of a Perfusor pump for the concentrate and infusion pump for the diluting medium through the mixing apparatus so that a total volumetric flow of 434 ml/h is reached. This reduces the concentration of the organic solvent macrogol 400 in the complete mixture to 7%. The infusion volume needed to administer the daily dose of 1000 mg of Bay 17-1648 in this case is 2×463.5 ml/day. The infusion time for a total of 1000 mg Bay 17-1648 in this case is 2×64 min.

| Mixer type | — | B |
|---|---|---|
| Inlet pressure: diluting medium (DM) | mbar | 100 |
| Inlet pressure: active ingredient concentrate (AC) | mbar | 170 |
| Solvent concentration (CM) | g/100 ml[1] | 7 |
| Active ingredient concentration in the solvent | g/100 ml[2] | 1.5 |
| Total amount of infused solvent | ml | 67 |
| Diluting medium | — | water |
| Volume of the complete mixture (CM) | ml | 927 |
| Metering rate (total active ingredient dose) | mg/min | 1000 mg/128 min |
| Volumetric flow CM | ml/h | 434 |
| Flow velocity: AC nozzle | m/s | 0.18 |
| Flow velocity: DM nozzle | m/s | 2.28 |
| Flow velocity: CM aperture | m/s | 2.46 |
| Particle count ≧ 10 μm [max. 25/ml] | Particle count/ml | 19 |
| Particle count ≧ 25 μm [max. 3/ml] | Particle count/ml | 2 |

[1] Mass of solvent based on 100 ml of complete solution;
[2] Mass of active ingredient based on 100 ml of solvent (active ingredient concentrate).

The saturation solubility of Bay 17-1648 with 7% PEG in water is about 70 mg/100 ml. Compared with this value, the mixture ready for use is a factor of 1.5 supersaturated at 108 mg/100 ml. As the particle measurements show, the formulation is stable to crystallization for at least 1 min.

EXAMPLE 4

Formulation of an Antibiotic of the Oxazolidinone Class (Bay 34-7780) as 5% Strength Aqueous Active Ingredient Concentrate with Acidic pH The antibiotic Bay 34-7780 ((5S)-3-[2-(3-pyridyl) pyridin-5-yl]-5-(methoxycarbonyl-aminomethyl) oxazolidin-2-one hydrochloride, EP-789026) as hydrochloride has a highly pH-dependent solubility which allows only an acidic (pH 2.5) active ingredient concentrate to be formulated. The saturation concentrations are as follows:

| pH | Saturation concentration |
|---|---|
| 2.5 | 110 g/l |
| 4 | 0.4 g/l |

Formulation of a tolerated aqueous infusion solution with a pH of 4.0 would accordingly be associated with an infusion volume of at least 2.5 l for a daily dose of 1000 mg.

The only formulation which can be prepared for the desired daily dose of 1000 mg with a maximum infusion volume of 500 ml has pH 2.5. This must be adjusted to a pH of at least 4.0 before administration. Exceeding the saturation concentration by a factor of 5 in this case results in crystallization after standing for a short time.

The pKa of the active ingredient is 4.2 for a moderately strong acid. Utilization of 50% of the acid by addition of base adjusts the pH in accordance with the Henderson-Hasselbalch equation to correspond to the pKa of 4.2.

On use according to the invention of the mixing apparatus, 20 ml of 5% strength aqueous active ingredient concentrate pH 2.5 and 480 ml of sodium hydroxide solution pH 10.5 (ratio 1:24) are combined by means of a Perfusor pump for the concentrate and infusion pump for the diluting medium through the mixing apparatus so that a total volumetric flow of 500 ml/h is reached. This adjusts the pH of the solution to about pH 4. The infusion volume needed to administer the daily dose of 1000 mg of Bay 34-7780 is 500 ml/day. The infusion time in this case is 60 min for 1000 mg of Bay 34-7780.

The saturation solubility of Bay 34-7780 at pH 4 is about 40 mg/100 ml. Compared with this value, the mixture ready for use is a factor of 5 supersaturated at 200 mg/100 ml. A solution with a sufficiently well-tolerated pH can be administered by the use according to the invention of the homogenizing apparatus.

| Mixer type | — | B |
|---|---|---|
| Inlet pressure: dilutin medium (DM) | mbar | 120 |
| Inlet pressure: active ingredient concentrate (AC) | mbar | <100 |
| Active ingredient concentration in the solvent | g/100 ml[1] | 5 |
| Total amount of infused solvent | ml | 20 (pH 2.5) |
| Dilutin medium | — | NaOH (pH 10.5) |
| Volume of the complete mixture (CM) | ml | 500 |
| Metering rate (total active ingredient dose) | mg/min | 1000 mg/60 min |
| Volumetric flow CM | ml/h | 500 |
| Flow velocity: AC nozzle | m/s | 0.11 |
| Flow velocity: DM nozzle | m/s | 2.72 |
| Flow velocity: CM aperture | m/s | 2.83 |
| Particle count ≧ 10 μm [max. 25/ml] | Particle count/ml | 17 |
| Particle count ≧ 25 μm [max. 3/ml] | Particle count/ml | 1 |

[1] Mass of active ingredient based on 100 ml of solvent (active ingredient concentrate).

EXAMPLE 5

Formulation of a Dihydropyridine (Bay y 5959, Ca Promoter) with Macrogol 400 as 0.5% Strength and 0.2% Strength Active Ingredient Concentrate The dihydropyridine Bay y 5959 (isopropyl (−)-(R)-2-amino-5-cyano-1,4-dihydro-6-methyl-4-(3-phenylquinolin-5-yl)pyridine-3-carboxylate, Ca promoter, EP-0 515 940 A1) is very slightly soluble in water at about 0.1 μg/100 ml, but is readily soluble in macrogol 400 (PEG) at about 10 g/100 ml.

Although a 30% strength PEG solution with an active ingredient content of 100 mg/100 ml prepared in the conventional way without using the method according to the invention and apparatus according to the invention is stable to crystallization for 12 hours, therapeutic use of Bay y 5959 requires repeated administration over a period of 5 days. The 30% concentration of PEG proved to be poorly tolerated by veins on this long-term use. It is therefore necessary to limit the concentration of organic solvents in the mixture for administration to a maximum of about 15% PEG.

| | |
|---|---|
| Solvent concentration | 30% PEG |
| Diluting medium | water |
| Active ingredient saturation conc. in CM | ca. 4 mg/100 ml (0.004%) |
| Active ingredient concentration in CM | 100 mg/100 ml (0.1%) |
| Supersaturation in CM | ca. 25-fold |
| Amount of solvent per dose | 30 g/100 mg |
| Crystallization | after 12 h |

EXAMPLE 5.1

On use according to the invention of the mixing apparatus, 20 ml of 0.5% strength active ingredient concentrate and 100 ml of water (ratio 1:5) are combined by means of a Perfusor pump for the concentrate and infusion pump for the diluting medium through the mixing apparatus so that a total volumetric flow of 180 ml/h is reached. This reduces the concentration of the organic solvent macrogol 400 in the complete mixture to 16.7%. The infusion volume needed to administer the dose of 100 mg of Bay y 5959 in this case is 120 ml. The infusion time in this case is 40 min for 100 mg of Bay y 5959.

| | | |
|---|---|---|
| Mixer type | — | B |
| Inlet pressure: diluting medium (DM) | mbar | <100 |
| Inlet pressure: active ingredient concentrate (AC) | mbar | <100 |
| Solvent concentration (CM) | g/100 ml[1] | 16.7 |
| Active ingredient concentration in the solvent | g/100 ml[2] | 0.5 |
| Total amount of infused solvent | ml | 20 |
| Diluting medium | — | water |
| Volume of the complete mixture (CM) | ml | 120 |
| Metering rate (total active ingredient dose) | mg/min | 100 mg/40 min |
| Volumetric flow CM | ml/h | 180 |
| Flow velocity: AC nozzle | m/s | 0.17 |
| Flow velocity: DM nozzle | m/s | 0.85 |
| Flow velocity: CM aperture | m/s | 1.02 |
| Particle count $\geq$ 10 µm [max. 25/ml] | Particle count/ml | 8 |
| Particle count $\geq$ 25 µm [max. 3/ml] | Particle count/ml | 1 |

[1] Mass of solvent based on 100 ml of complete solution;
[2] Mass of active ingredient based on 100 ml of solvent (active ingredient concentrate).

EXAMPLE 5.2

In another example, 50 ml of 0.2% strength active ingredient concentrate and 283 ml of water (ratio 1:5.7) are combined by means of a Perfusor pump for the concentrate and infusion pump for the diluting medium through the mixing apparatus so that a total volumetric flow of 200 ml/h is reached. This reduces the concentration of the organic solvent macrogol 400 in the complete mixture to 15%. The infusion volume needed to administer the dose of 100 mg of Bay y 5959 in this case is 333 ml. The infusion time in this case is 100 min for 100 mg of Bay y 5959.

| | | |
|---|---|---|
| Mixer type | — | B |
| Inlet pressure: diluting medium (DM) | mbar | <100 |
| Inlet pressure: active ingredient concentrate (AC) | mbar | <100 |
| Solvent concentration (CM) | g/100 ml[1] | 15 |
| Active ingredient concentration in the solvent | g/100 ml[2] | 0.2 |
| Total amount of infused solvent | ml | 50 |
| Diluting medium | — | water |
| Volume of the complete mixture (CM) | ml | 333 |
| Metering rate (total active ingredient dose) | mg/min | 100 mg/100 min |
| Volumetric flow CM | ml/h | 200 |
| Flow velocity: AC nozzle | m/s | 0.17 |
| Flow velocity: DM nozzle | m/s | 0.96 |
| Flow velocity: CM aperture | m/s | 1.13 |
| Particle count $\geq$ 10 µm [max. 25/ml] | Particle count/ml | 6 |
| Particle count $\geq$ 25 µm [max. 3/ml] | Particle count/ml | 1 |

[1] Mass of solvent based on 100 ml of complete solution;
[2] Mass of active ingredient based on 100 ml of solvent (active ingredient concentrate).

The supersaturation rates achieved with Bay y 5959 are as follows:

| Solvent (PEG) concentration | Active ingredient saturation concentration in CM | Active ingredient concentration in CM | Super-saturation in CM | PEG amount per 100 mg active ingredient dose |
|---|---|---|---|---|
| 30.0% | 0.0040 g/100 ml | 0.10 g/100 ml | 25-fold | 30 g |
| 16.7% | ca. 0.0012 g/100 ml | 0.08 g/100 ml | 67-fold | 21 g |
| 15.0% | ca. 0.0012 g/100 ml | 0.03 g/100 ml | 25-fold | 50 g |

CM = complete mixture

The use according to the invention of the apparatus allows up to 67-fold supersaturated infusion solutions to be used without the active ingredient crystallizing out in the administration system. In this case not only is the solvent concentration reduced with an improvement in the local tolerability, but there is also a distinct reduction in the amount of solvent per dose, which increases the systemic tolerability.

EXAMPLE 6

Formulation of the Dihydropyridine Nifedipine (Adalat®) with Macrogol 400 as 0.2% Strength Active Ingredient Concentrate Nifedipine is commercially available as an i.v. formulation as 0.01% strength aqueous solution with 15% ethanol and 15% macrogol 400 (PEG). The formulation is based on the low solubility of nifedipine in water. The use of ethanol and PEG means that the tolerability is not optimal, and approval in Japan is impossible because of the ethanol content.

| | |
|---|---|
| Solvent concentration | 30% (15% PEG + 15% ethanol) |
| Diluting medium | water |
| Active ingredient saturation conc. in CM | ca. 42 mg/100 ml (0.042%) |
| Active ingredient concentration in CM | 10 mg/100 ml (0.1%) |
| Supersaturation in CM | none |
| Amount of solvent per dose | 15 g/5 mg (7.5 g PEG + 7.5 g ethanol) |
| Crystallization | none |

The use according to the invention of the mixing apparatus makes it possible, on formulating analogously to Example 5, to employ a solution of nifedipine in PEG and to dispense with ethanol.

2.5 ml of 0.2% strength active ingredient concentrate and 25.5 ml of water (ratio 1:10) are combined by means of two Perfusor pumps through the mixing apparatus so that a total volumetric flow of 6.6 ml/h is reached. This reduces the concentration of the organic solvent PEG in the complete mixture to 8.9%. The infusion volume needed to administer the dose of 5 mg of nifedipine is 28 ml, in which case the infusion time is 255 min, equivalent to a therapeutic dosage rate of about 1.2 mg/h.

| Mixer type | — | A |
|---|---|---|
| Inlet pressure: diluting medium (DM) | mbar | <100 |
| Inlet pressure: active ingredient concentrate (AC) | mbar | <100 |
| Solvent concentration (CM) | g/100 ml[1] | 8.9 |
| Active ingredient concentration in the solvent | g/100 ml[2] | 0.2 |
| Total amount of infused solvent | ml | 2.5 |
| Diluting medium | — | water |
| Volume of the complete mixture (CM) | ml | 28 |
| Metering rate (total active ingredient dose) | mg/min | 5 mg/255 min |
| Volumetric flow CM | ml/h | 6.6 |
| Flow velocity: AC nozzle | m/s | 0.02 |
| Flow velocity: DM nozzle | m/s | 0.21 |
| Flow velocity: CM aperture | m/s | 0.23 |
| Particle count ≧ 10 μm [max. 25/ml] | Particle count/ml | 12 |
| Particle count ≧ 25 μm [max. 3/ml] | Particle count/ml | 1 |

[1]Mass of solvent based on 100 ml of complete solution;
[2]Mass of active ingredient based on 100 ml of solvent (active ingredient concentrate).

It is possible in this case to obtain, after dilution to the use concentration by using the apparatus, a 0.02% strength solution, that is to say twice as concentrated as the commercial formulation. A further advantage is the possibility of achieving a solvent concentration of 8.9%; this corresponds to a concentration reduction to one-third relative to the commercial formulation. On use of the invention it is necessary to infuse per 5 mg dose of nifedipine only 2.5 ml of macrogol 400 compared with 7.5 g of macrogol and 7.5 g of ethanol for the commercial product.

It was possible to show on the basis of the examples that the present invention has the following advantages:

1. Possibility of parenteral administration of slightly soluble pharmaceuticals in high concentrations.
2. Possibility of reliable, reproducible and safe administration of supersaturated infusion solutions with which there is a great tendency to crystallization of the active ingredient by in situ formulation.
3. Avoidance of the problem of the stability of supersaturated solutions.
4. Mixing of fluids at extremely low volumetric flows.
5. Mixing of fluids differing considerably in viscosity at low volumetric flows.
6. Reduction in the amount of excipients administered.
7. Complete avoidance of excipients or reduction in the concentration thereof.
8. Reduction in the volume of organic solvents infused.
9. The small dimensions of the apparatus of the invention make direct attachment to the patient possible.

What is claimed is:

1. A method for the in situ formulation of a medicinal substance solution for parenteral administration, comprising continuously combining at least two metered part-streams with the aid of a mixer to produce an active ingredient-containing solution as a total volumetric flow, characterized in that said solution is not in thermodynamic equilibrium, and said total volumetric flow after mixing is 0.2 ml/h to 500 ml/h.

2. The method according to claim 1, wherein the mixer includes a mixing chamber having a volume of 0.2 μl to 2 μl.

3. The method according to claim 2, wherein said mixer further comprises a mixing section located downstream from said mixing chamber, and the time spent by the active ingredient containing solution in said mixing section is less than 10 min.

4. The method according to claim 3, wherein said time spent by the active ingredient containing solution in said mixing section is less than 5 min.

5. The method according to claim 2, wherein said mixing chamber has a volume of 0.4 μl to 1.5 μl.

6. The method according to claim 1, wherein the metered part-streams comprise at least one active ingredient-containing solution and at least one active ingredient-free diluting medium, and the solution which is not in thermodynamic equilibrium is a supersaturated solution.

7. The method according to claim 6, wherein the active ingredient-containing solution is an organic or aqueous organic active ingredient concentrate, and the diluting medium is an aqueous or aqueous organic diluting medium.

8. The method according to claim 6, wherein said active ingredient containing solution is an aqueous or aqueous organic active ingredient concentrate, said active ingedient-free diluting medium is an aqueous or aqueous organic diluting medium, and the pH values of said concentrate and said diluting medium are matched together so that the total volumetric flow resulting after the mixing has a physiologically tolerated pH in the range from 3 to 10.

9. The method according to claim 8, wherein said total volumetric flow resulting after the mixing has a physiologically tolerated pH in the range from 5–8.

10. The method according to claim 6, wherein said active ingredient containing solution has a viscosity ≦500 mPa.s and said aqueous active ingredient-free diluting medium has a viscosity in the range from 1 mPa.s to 0 mPa.s.

11. The method according to claim 10, wherein active ingredient containing solution has a viscosity in the range from 50 mPa.s to 150 mPa.s and said aqueous active ingredient-free diluting medium has a viscosity in the range from 1 mPa.s to 10 mPa.s.

12. The method according to claim 1, wherein one part-stream contains active ingredient having a solubility of less than 1% by weight in water at 20° C.

13. The method according to claim 1, wherein the active ingredient is selected from the group consisting of dihydropyridines, anaesthetics, antibiotics, antimycotics, immunosuppressants, CNS-active drugs, oncologicals, steroids, barbiturates and vitamins.

14. The method according to claim 1, wherein paclitaxel, docetaxel or substances related thereto, or cyclosporin, is used as active ingredient.

15. The method according to claim 1, wherein said mixer is without dead spaces.

16. The method according to claim 1, wherein said mixer is a nozzle mixer which comprises a) at least one set of opposing nozzles, each of said nozzles having a hydraulic diameter between 1 μm and 500 μm; b) a mixing chamber between said nozzles and having a volume of 0.2 μl to 2.0 μl; and c) a homogenizing aperture located downstream from and adjacent to said mixing chamber and having a hydraulic diameter between 1 µm and 500 µm; whereby each of said part-streams collides with the other in said mixing chamber, and the resulting active ingredient containing solution moves through said homogenizing aperture as said total volumetric flow.

17. The method according to claim 16, wherein the nozzle diameter is chosen so that the flow velocity in the nozzles is 0.01 to 15 m/s.

18. The method according to claim 17, wherein said nozzle diameter is chosen so that the flow velocity in the nozzles is 0.0 to 3 m/s.

19. The method according to claim 16, wherein said nozzles have a hydraulic diameter between 100 µm and 250 µm.

20. The method according to claim 1, wherein said resulting total volumetric flow after mixing is 5 ml/h to 500 ml/h.

21. Apparatus for the in situ formulation of an active ingredient solution for parental administration, comprising a nozzle mixer which includes: a) a first inlet, in the form of a nozzle having a hydraulic diameter between 1 µm and 500 µm; b) a homogenizing aperture located downstream of said first inlet and having a hydraulic diameter between 1 µm and 500 µm; c) a mixing chamber between said first inlet and said homogenizing aperture, and having a volume of 0.2 µl to 2 µl; d) at least one inlet to said mixing chamber in addition to said first inlet; and e) a mixing section located downstream of said homogenizing aperture and connected to it.

22. The apparatus according to claim 21 further comprising at least two feed lines, in each of which a reservoir and a metering device are connected in series, each of said feed lines being connected to an inlet of said nozzle mixer; and an infusion line downstream of said nozzle mixer and connected to said mixing section thereof.

23. The apparatus according to claim 22, wherein the flow pathways in the two feed lines, including the metering devices and the nozzles, are symmetrically designed.

24. The apparatus according to claim 21, wherein the mixer is made of an injection-moldable plastic.

25. The apparatus according to claim 21, wherein said homogenizing aperture of the mixer is opposite to said nozzle.

26. The apparatus according to claim 21 wherein the additional inlet to said mixing chamber is in the form of a nozzle having a hydraulic diameter of 1 µm to 500 µm.

27. The apparatus according to claim 21, wherein said mixing chamber has a volume of 0.4 µl to 1.5 µl, and said nozzle has a hydraulic diameter of 100 µm to 250 µm.

28. The apparatus according to claim 21, wherein said homogenizing aperture has a hydraulic diameter of 100 µm to 250 µm.

29. The apparatus according to claim 21, wherein said mixer is made of polycarbonate.

30. An active ingredient administration kit for carrying out the method according to claim 1, comprising apparatus according to claim 21 and a reservoir with active ingredient concentrate.

31. The active ingredient administration kit according to claim 30, further comprising a reservoir with diluting medium.

32. The active ingredient administration kit according to claim 30, wherein further comprising tubing for the connections to the apparatus and to the metering devices.

33. The active ingredient administration kit according to claim 30, in which the active ingredient has a solubility of less than 1% by weight in water at 20° C.

34. The active ingredient administration kit according to claim 30, in which the active ingredient is selected from the group consisting of dihydropyridines, anaesthetics, antibiotics, antimycotics, immunosuppressants, CNS-active drugs, oncologicals, steroids, barbiturates and vitamins.

35. An active ingredient administration kit according to claim 34, in which said active ingredient is paclitaxel, docetaxel or substances related thereto.

36. The active ingredient administration kit according to claim 34, in which said active ingredient is cyclosporin.

\* \* \* \* \*